(12) United States Patent
Chen (10) Patent No.: US 10,828,210 B1
(45) Date of Patent: Nov. 10, 2020

(54) URINE CONTAINMENT DEVICE

(71) Applicant: Frank Chen, San Marino, CA (US)

(72) Inventor: Frank Chen, San Marino, CA (US)

( * ) Notice: Subject to any disclaimer, the term of this patent is extended or adjusted under 35 U.S.C. 154(b) by 703 days.

(21) Appl. No.: 15/652,410

(22) Filed: Jul. 18, 2017

(51) Int. Cl.
*A61F 13/74* (2006.01)
*A61F 13/72* (2006.01)
*A61F 5/44* (2006.01)
*A61F 5/449* (2006.01)
*A61F 5/453* (2006.01)

(52) U.S. Cl.
CPC .............. *A61F 13/74* (2013.01); *A61F 13/72* (2013.01); *A61F 5/4408* (2013.01); *A61F 5/449* (2013.01); *A61F 5/453* (2013.01)

(58) Field of Classification Search
CPC ........ A61F 13/74; A61F 13/72; A61F 5/4408; A61F 5/449; A61F 5/453; A41B 9/026
USPC .......................................................... 604/391
See application file for complete search history.

(56) References Cited

U.S. PATENT DOCUMENTS

| | | | |
|---|---|---|---|
| 4,820,291 A * | 4/1989 | Terauchi | A61F 5/451 4/144.3 |
| 4,846,816 A | 7/1989 | Manfredi | |
| 5,797,890 A | 8/1998 | Goulter | |
| 5,935,116 A * | 8/1999 | Kristensen | A61F 5/4408 604/353 |
| 6,059,762 A | 5/2000 | Boyer | |
| D467,338 S | 12/2002 | Rehrig | |
| 7,077,833 B2 | 7/2006 | Bonham | |
| 7,658,730 B2 | 2/2010 | Conley | |
| 8,702,667 B1 * | 4/2014 | Johnson | A61F 13/471 604/349 |
| 9,737,433 B2 * | 8/2017 | Joh | A61F 5/451 |
| 2015/0173974 A1 * | 6/2015 | Delija | A61F 13/505 604/385.15 |
| 2016/0278438 A1 * | 9/2016 | Polidan | A41B 9/023 |

FOREIGN PATENT DOCUMENTS

WO 2004071361 A 8/2004

* cited by examiner

*Primary Examiner* — Andrew J Mensh (57) ABSTRACT

The urine containment device is an item of underclothing. The urine containment device is worn by a man. The urine containment device is designed to receive and store urine seepage from the man. The urine containment device is formed with a right pocket and a left pocket. The right and right pockets: 1) contain an absorbent pad; and, 2) are each formed with an opening such that the penis of the man may be privately inserted into the selected pocket such that the absorbent pad will absorb any urine seepage that may be generated. The urine containment device comprises a posterior panel, a right panel, a left panel, a pocket panel, a waist band, and a plurality of seams. The posterior panel, the right panel, the left panel, the pocket panel, the waist band are assembled to form the urine containment device using the plurality of seams.

16 Claims, 7 Drawing Sheets

URINE CONTAINMENT DEVICE

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of medical and veterinary sciences including dressings and absorbent pads, more specifically, a device worn by a patient for receiving urine.

SUMMARY OF INVENTION

The urine containment device is an item of underclothing. The urine containment device is worn by a man. The urine containment device is designed to receive and store urine seepage from the man. The urine containment device is formed with a right pocket and a left pocket. The right pocket: 1) contains a right absorbent pad; and, 2) is formed with a right opening such that the penis of the man may be privately inserted into the right pocket such that the absorbent pad will absorb any urine seepage that may be generated. The left pocket: 1) contains a left absorbent pad; and, 2) is formed with a left opening such that the penis of the man may be privately inserted into the left pocket such that the absorbent pad will absorb any urine seepage that may be generated. The urine containment device comprises a posterior panel, a right panel, a left panel, a pocket panel, a waist band, and a plurality of seams. The posterior panel, the right panel, the left panel, the pocket panel, the waist band are assembled to form the urine containment device using the plurality of seams.

These together with additional objects, features and advantages of the urine containment device will be readily apparent to those of ordinary skill in the art upon reading the following detailed description of the presently preferred, but nonetheless illustrative, embodiments when taken in conjunction with the accompanying drawings.

In this respect, before explaining the current embodiments of the urine containment device in detail, it is to be understood that the urine containment device is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the urine containment device.

It is therefore important that the claims be regarded as including such equivalent construction insofar as they do not depart from the spirit and scope of the urine containment device. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

FIG. 3 is a cross-sectional view of an embodiment of the disclosure across 4-4 as shown in FIG. 1.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
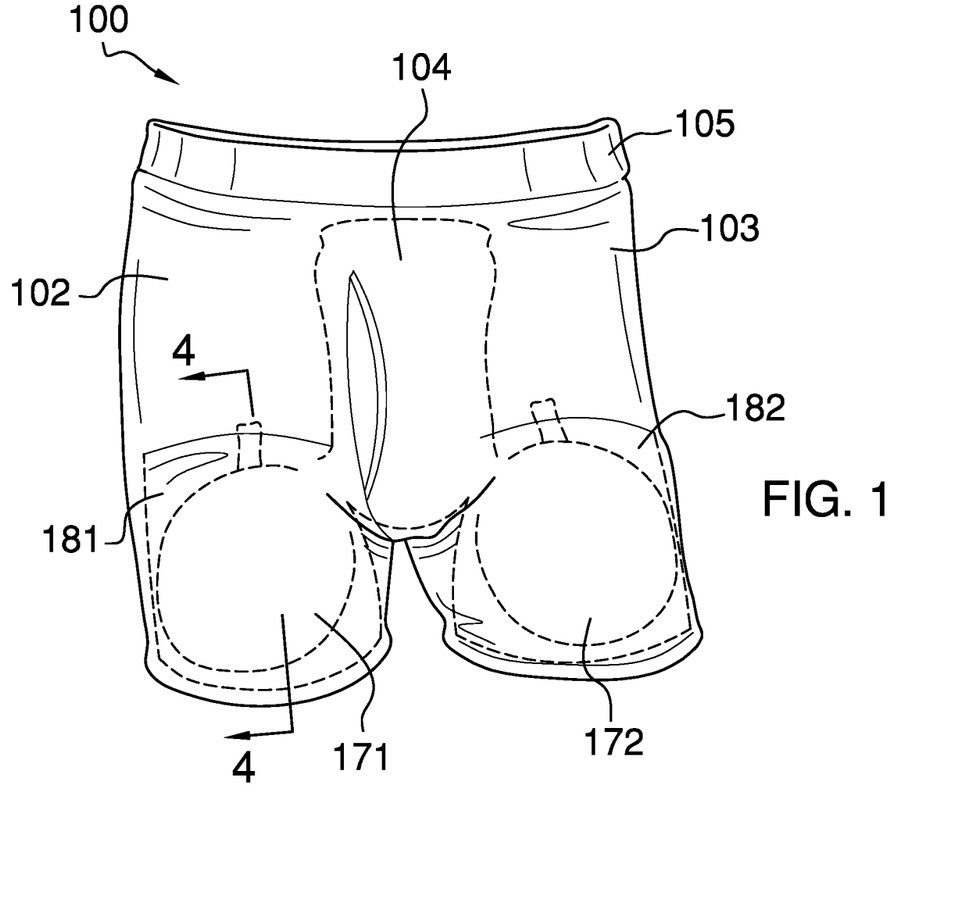
FIG. 1 is a perspective view of an embodiment of the disclosure.
Figure 2:
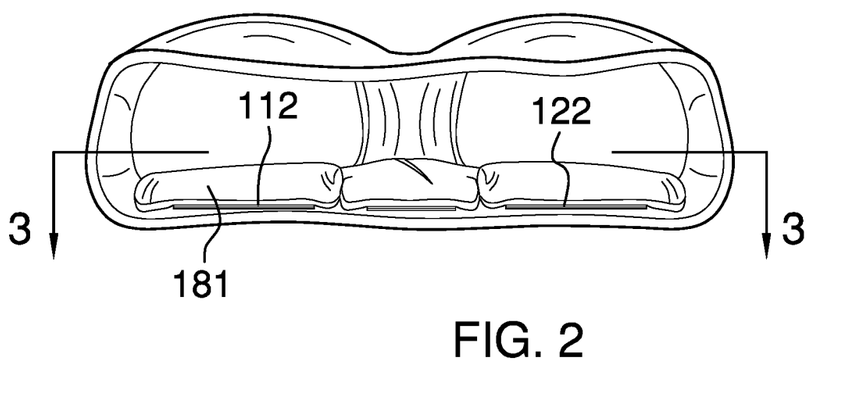
FIG. 2 is a top view of an embodiment of the disclosure.
Figure 3:
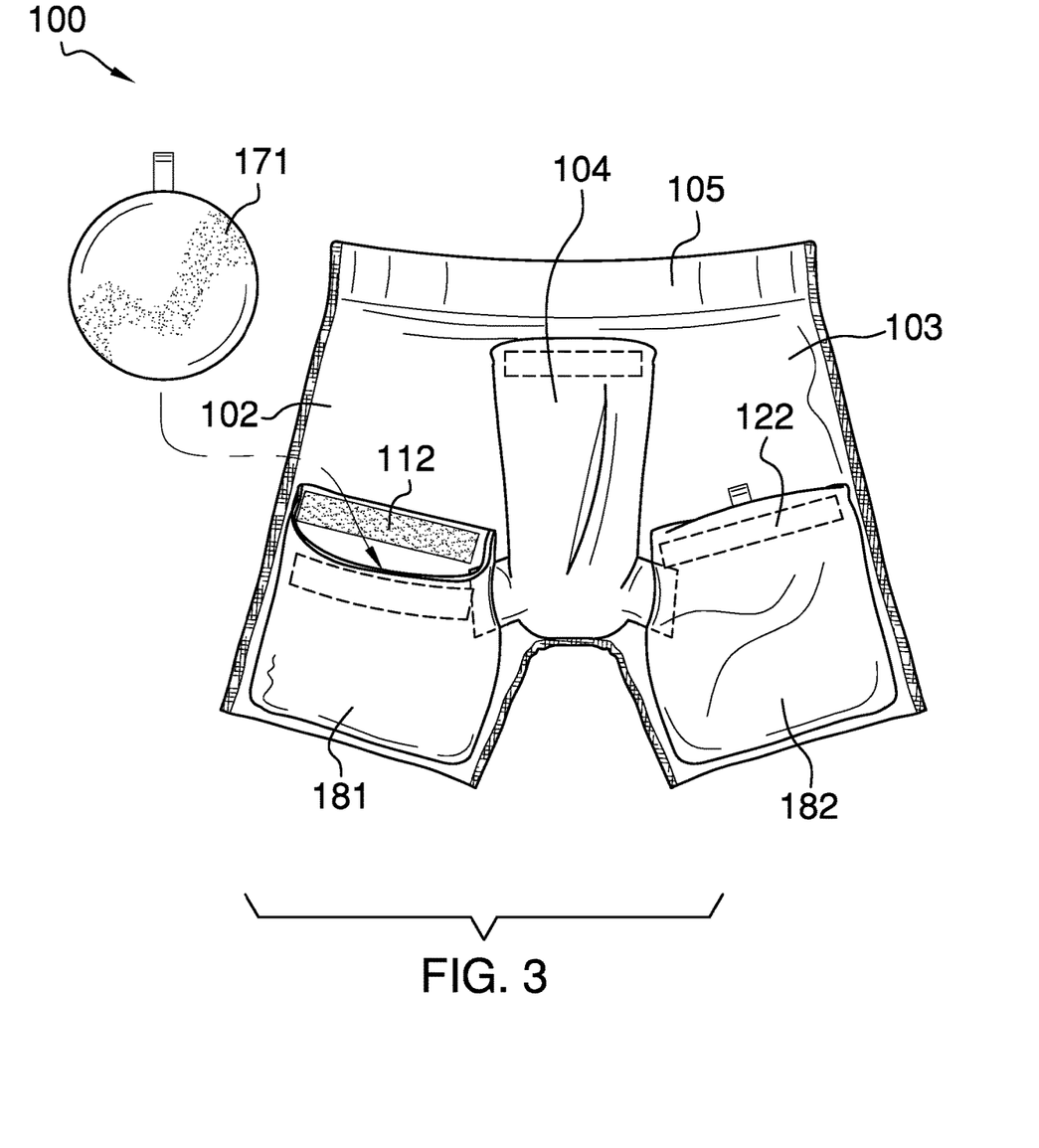
FIG. 3 is a cross-sectional view of an embodiment of the disclosure across 3-3 as shown in FIG. 2.
Figure 4:
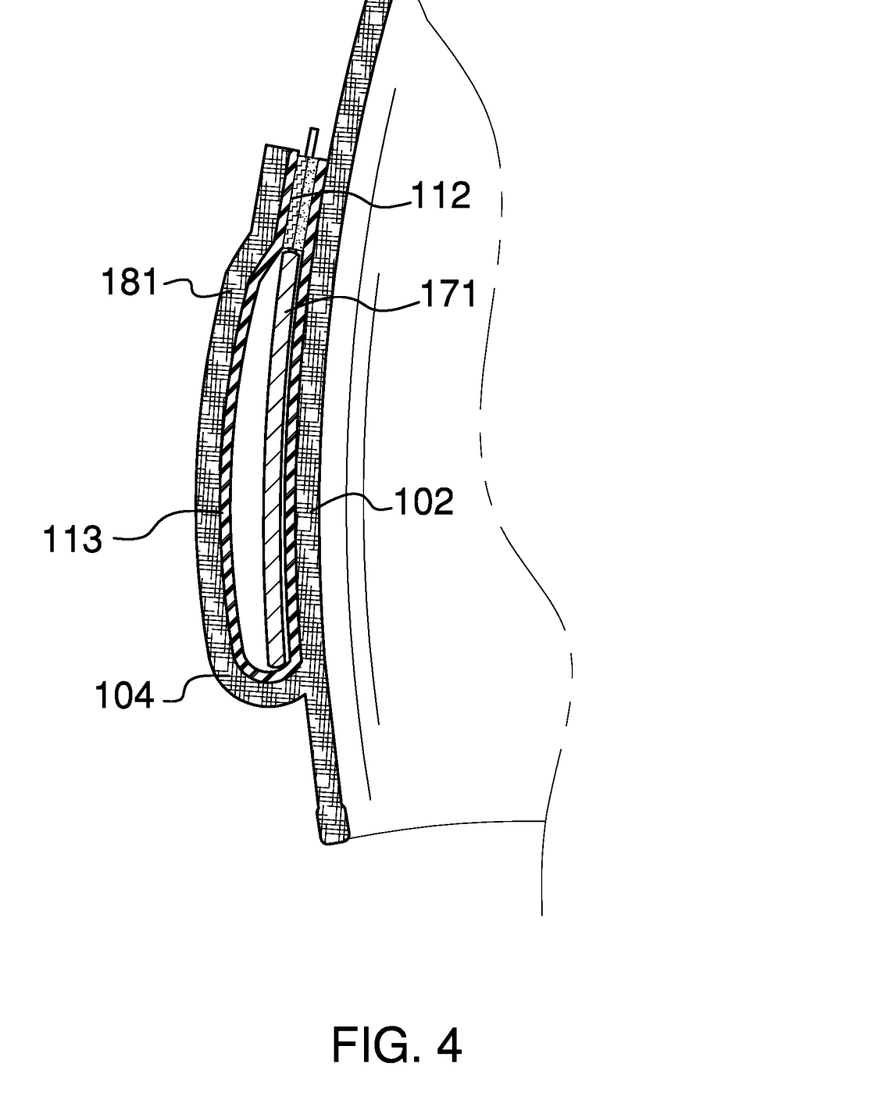
Figure 5:
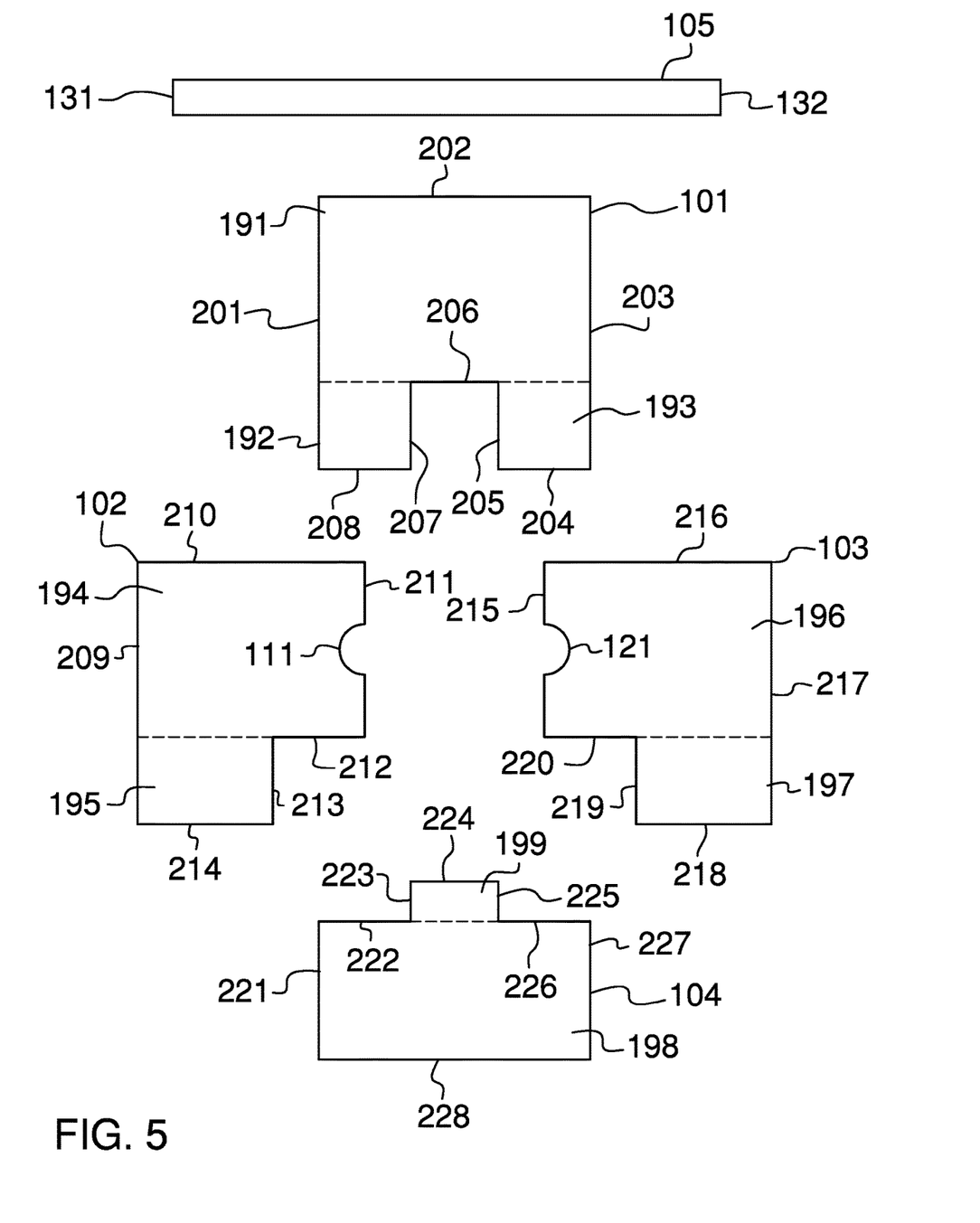
FIG. 5 is a detail view of an embodiment of the disclosure.
Figure 6:
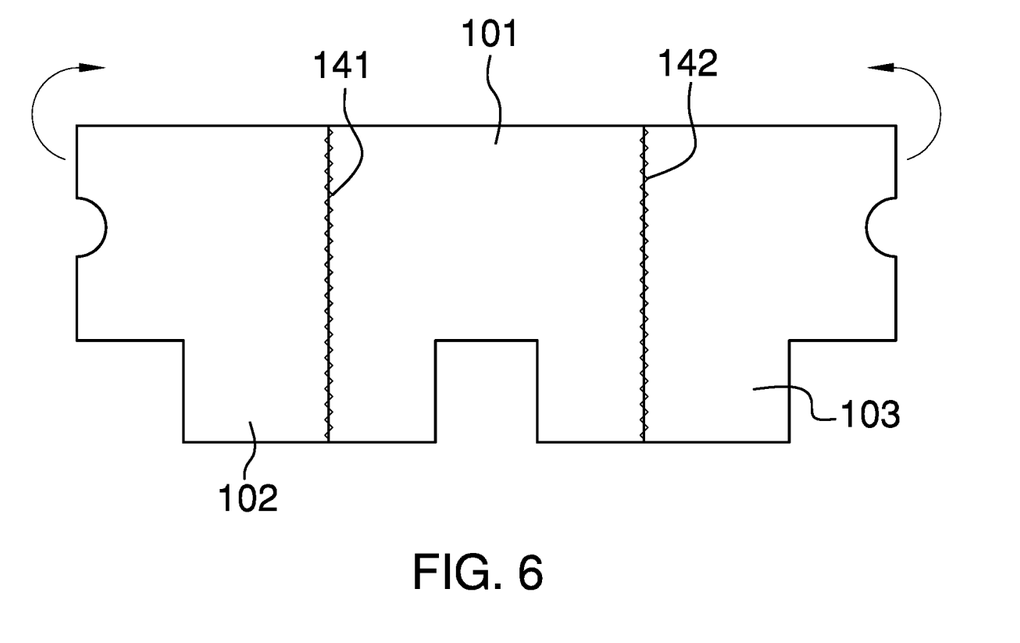
FIG. 6 is a detail view of an embodiment of the disclosure.
Figure 7:
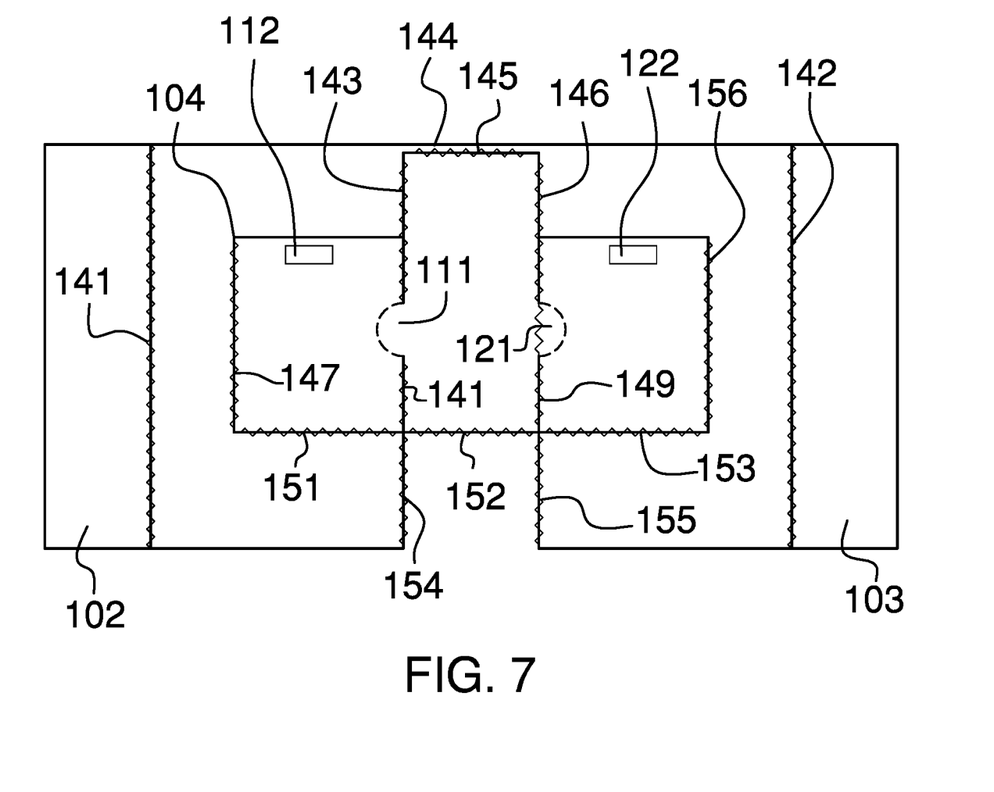
FIG. 7 is a detail view of an embodiment of the disclosure.
Figure 8:
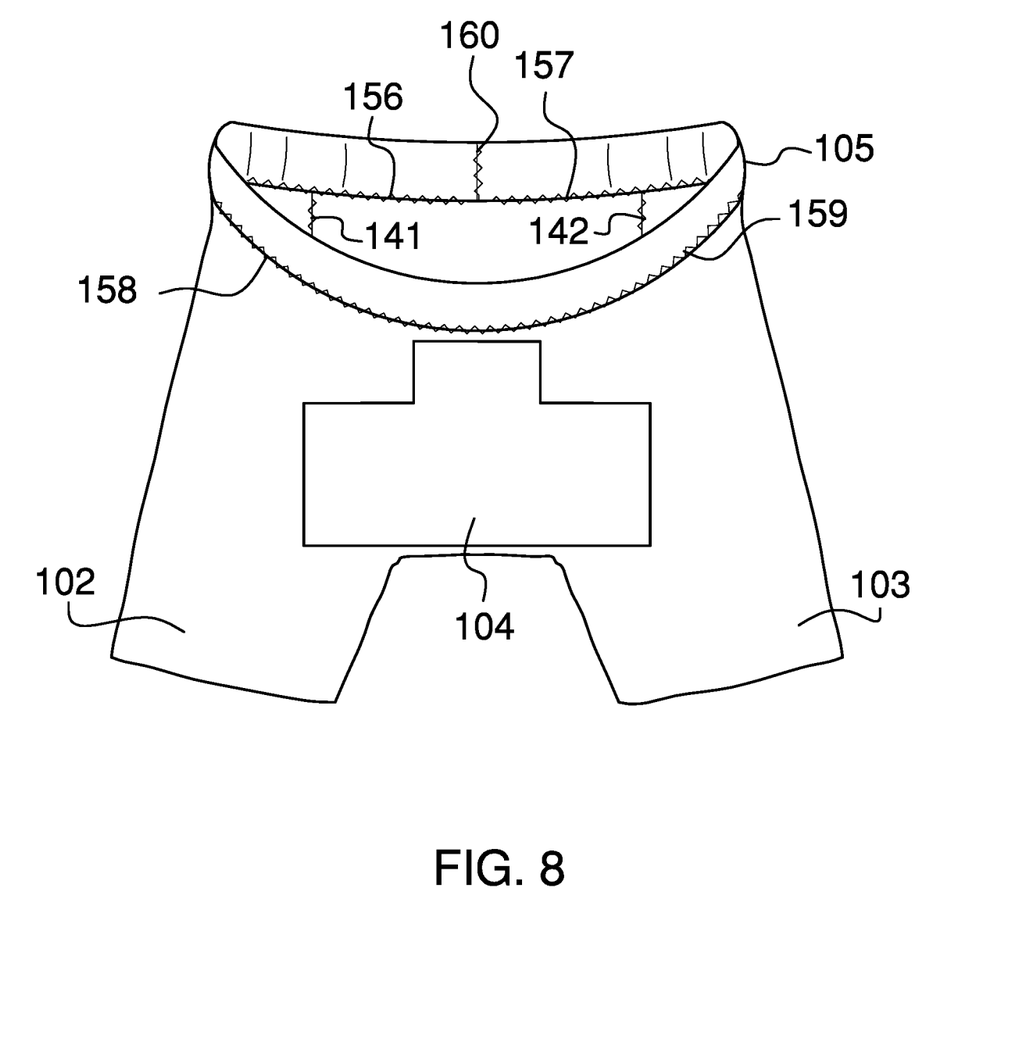
FIG. 8 is a detail view of an embodiment of the disclosure.

Detailed reference will now be made to one or more potential embodiments of the disclosure, which are illustrated in FIGS. 1 through 8.

The urine containment device 100 (hereinafter invention) is an item of underclothing. The invention 100 is worn by a man. The man is further defined with a loin. The invention 100 is designed to receive and store urine seepage from the man. The invention 100 is formed with a right pocket 181 and a left pocket 182. The right pocket 181: 1) contains a right absorbent pad 171; and, 2) is formed with a right opening such that the penis of the man may be privately inserted into the right pocket 181 such that the right absorbent pad 171 will absorb any urine seepage that may be generated. The left pocket 182: 1) contains a left absorbent pad 172; and, 2) is formed with a left opening such that the penis of the man may be privately inserted into the left pocket 182 such that the left absorbent pad 172 will absorb any urine seepage that may be generated. The invention 100 comprises a posterior panel 101, a right panel 102, a left panel 103, a pocket panel 104, a waist band 105, and a plurality of seams. The posterior panel 101, the right panel 102, the left panel 103, the pocket panel 104, the waist band 105 are assembled to form the invention 100 using the plurality of seams.

The posterior panel 101 is a readily and commercially available textile that is cut in a rectilinear shape. The posterior panel 101 covers the posterior region of the loin. The posterior panel 101 is further defined by a first block 191, a second block 192, and a third block 193. The posterior panel 101 is further defined with a first edge 201, a second edge 202, a third edge 203, a fourth edge 204, a fifth edge 205, a sixth edge 206, a seventh edge 207, and an eighth edge 208.

The first block 191 is a rectangular subsection of the posterior panel 101. The first block 191 covers the posterior region of the loin. The first block 191 is partially bounded by the first edge 201, the second edge 202, the third edge 203, and the sixth edge 206. The second block 192 is a rectangular subsection of the posterior panel 101. The second block 192 covers the upper right leg. The second block 192 is partially bounded by the first edge 201, the seventh edge 207, and the eighth edge 208. The third block 193 is a rectangular subsection of the posterior panel 101. The third block 193 covers the upper left leg. The third block 193 is partially bounded by the third edge 203, the fourth edge 204, and the fifth edge 205.

The right panel 102 is a readily and commercially available textile that is cut in a rectilinear shape. The right panel 102 covers the right side and a portion of the anterior region of the loin.

The right panel 102 is further defined by a fourth block 194 and a fifth block 195. The right panel 102 is further defined with a ninth edge 209, a tenth edge 210, an eleventh edge 211, a twelfth edge 212, a thirteenth edge 213, and a fourteenth edge 214.

The fourth block 194 is a rectangular subsection of the right panel 102. The fourth block 194 covers the right side and a portion of the anterior of the loin. The fourth block 194 is partially bounded by the ninth edge 209, the tenth edge 210, the eleventh edge 211, and the twelfth edge 212. The fifth block 195 is a rectangular subsection of the right panel 102. The fifth block 195 covers the upper right leg. The fifth block 195 is partially bounded by the ninth edge 209, the thirteenth edge 213, and the fourteenth edge 214.

The right panel 102 comprises a right interior arch 111. The right interior arch 111 is formed in the eleventh edge 211. The right interior arch 111 is a negative space that is formed in the right panel 102. The right interior arch 111 is formed in the shape of an interior arch. The right interior arch 111 forms an opening through which the penis may be inserted into the right pocket 181.

The left panel 103 is a readily and commercially available textile that is cut in a rectilinear shape. The left panel 103 covers the left side and a portion of the anterior region of the loin. The left panel 103 is further defined by a sixth block 196 and a seventh block 197. The left panel 103 is further defined with a fifteenth edge 215, a sixteenth edge 216, a seventeenth edge 217, an eighteenth edge 218, a nineteenth edge 219, and a twentieth edge 220.

The sixth block 196 is a rectangular subsection of the left panel 103. The sixth block 196 covers the left side and a portion of the anterior of the loin. The sixth block 196 is partially bounded by the fifteenth edge 215, the sixteenth edge 216, the seventeenth edge 217, and the twentieth edge 220. The seventh block 197 is a rectangular subsection of the left panel 103. The seventh block 197 is used to cover the upper left leg. The seventh block 197 is partially bounded by the nineteenth edge 219, the eighteenth edge 218, and the nineteenth edge 219.

The left panel 103 comprises a left interior arch 121. The left interior arch 121 is formed in the fifteenth edge 215. The left interior arch 121 is a negative space that is formed in the left panel 103. The left interior arch 121 is formed in the shape of an interior arch. The left interior arch 121 forms an opening through which the penis may be inserted into the left pocket 182.

The pocket panel 104 is a readily and commercially available textile that is cut in a rectilinear shape. The pocket panel 104 attaches to the right panel 102 and the left panel 103 to form the right pocket 181 and the left pocket 182. The pocket panel 104 is further defined by an eighth block 198 and a ninth block 199. The pocket panel 104 is further defined with a twenty first edge 221, a twenty second edge 222, a twenty third edge 223, a twenty fourth edge 224, a twenty fifth edge 225, a twenty sixth edge 226, a twenty seventh edge 227, and a twenty eighth edge 228.

The eighth block 198 is a rectangular subsection of the pocket panel 104. The eighth block 198 forms the right pocket 181 and the left pocket 182 of the garment. The eighth block 198 is partially bounded by the twenty first edge 221, the twenty second edge 222, the twenty sixth edge 226, the twenty seventh edge 227, and the twenty eighth edge 228. The ninth block 199 is a rectangular subsection of the pocket panel 104. The ninth block 199 attaches to the right panel 102 and the left panel 103 for several structural purposes including offsetting the right pocket 181 and the left pocket 182 from the superior edges of the right panel 102 and the left panel 103 respectively. The ninth block 199 is partially bounded by the twenty third edge 223, the twenty fourth edge 224, and the twenty fifth edge 225.

The right pocket 181 is a pouch that is formed on the right panel 102 for the purpose of storing the right absorbent pad 171 during normal use of the invention 100. The right absorbent pad 171 is a commercially available absorbent material that is used to absorb and store urine seepage. The right pocket 181 further comprises a right hook and loop fastener 112, a right waterproof lining 113, and a right absorbent pad 171.

The right hook and loop fastener 112 is a readily and commercially available hook and loop fastening device. The right hook and loop fastener 112 is used to secure the right absorbent pad 171 within the right pocket 181. Hook and loop fasteners are discussed in greater detail elsewhere in this disclosure. The right waterproof lining 113 is used to line the interior surfaces of the right pocket 181 for the purpose of preventing the leakage of urine from the right pocket 181. The right waterproof lining 113 is formed from a water impermeable plastic sheeting.

The left pocket 182 is a pouch that is formed on the left panel 103 for the purpose of storing the left absorbent pad 172 during normal use of the invention 100. The left absorbent pad 172 is a commercially available absorbent material that is used to absorb and store urine seepage. The left pocket 182 further comprises a left hook and loop fastener 122, a left waterproof lining, and a left absorbent pad 172.

The left hook and loop fastener 122 is a readily and commercially available hook and loop fastening device. The left hook and loop fastener 122 is used to secure the left absorbent pad 172 within the left pocket 182. Hook and loop fasteners are discussed in greater detail elsewhere in this disclosure. The left waterproof lining is used to line the interior surfaces of the left pocket 182 for the purpose of preventing the leakage of urine from the left pocket 182. The left waterproof lining is formed from a water impermeable plastic sheeting.

The waist band 105 is a readily and commercially available elastic webbing. The waist band 105 secures the invention 100 to the loin during normal use of the invention 100. The waist band 105 is further defined with a first end 131 and a second end 132.

Each of the plurality of seams is an individual seam that attaches a portion of a first structure selected from the group consisting of: 1) the posterior panel 101; 2) the right panel 102; 3) the left panel 103; 4) the pocket panel 104; and, 5) the waist band 105 to a portion of a second structure selected from the group consisting of: 6) the posterior panel 101; 7) the right panel 102; 8) the left panel 103; 9) the pocket panel 104; and, 10) the waist band 105. In the first potential embodiment of the disclosure, each of the plurality of seams is a sewn seams. Methods to form and use sewn seams are well known and documented in the apparel arts.

The assembly and structure of the invention 100 is discussed in the following 9 paragraphs.

The plurality of seams comprises a first seam 141, a second seam 142, a third seam 143, a fourth seam 144, a fifth seam 145, a sixth seam 146, a seventh seam 147, an eighth seam 148, a ninth seam 149, a tenth seam 150, an eleventh seam 151, a twelfth seam 152, a thirteenth seam 153, a fourteenth seam 154, a fifteenth seam 155, a sixteenth seam 156, a seventeenth seam 157, an eighteenth seam 158, a nineteenth seam 159, and a twentieth seam 160.

The first seam 141 attaches the first edge 201 of the posterior panel 101 to the ninth edge 209 of the right panel 102. The second seam 142 attaches the third edge 203 of the posterior panel 101 to the seventeenth edge 217 of the left panel 103.

The third seam 143 attaches the eleventh edge 211 of the fourth block 194 to the twenty third edge 223 of the ninth block 199. The fourth seam 144 attaches the twenty fourth edge 224 of the ninth block 199 to the tenth edge 210 of the fourth block 194. The fifth seam 145 attaches the twenty fourth edge 224 of the ninth block 199 to the sixteenth edge 216 of the sixth block 196. The sixth seam 146 attaches the twenty fifth edge 225 of the ninth block 199 to the fifteenth edge 215 of the sixth block 196.

The seventh seam 147 attaches the twenty first edge 221 of the eighth block 198 to the face of the right panel 102. The eighth seam 148 attaches the eleventh edge 211 of the fourth block 194 to the face of the pocket panel 104. The ninth seam 149 attaches the fifteenth edge 215 of the sixth block 196 to the face of the pocket panel 104. The tenth seam 150 attaches the twenty seventh edge 227 of the eighth block 198 to the face of the left panel 103.

The eleventh seam 151 attaches the twenty eighth edge 228 of the eighth block 198 to the face of the right panel 102. The twelfth seam 152 attaches the twenty eighth edge 228 of the eighth block 198 to the sixth edge 206 of the posterior panel 101. The thirteenth seam 153 attaches the twenty eighth edge 228 of the eighth block 198 to the face of the left panel 103. The fourteenth seam 154 attaches the seventh edge 207 of the second block 192 to the thirteenth edge 213 of the fifth block 195. The fifteenth seam 155 attaches the fifth edge 205 of the third block 193 to the nineteenth edge 219 of the seventh block 197.

The sixteenth seam 156 attaches the second edge 202 of the posterior panel 101 to the waist band 105 from the first seam 141 to the twentieth seam 160. The seventeenth seam 157 attaches the second edge 202 of the posterior panel 101 to the waist band 105 from the second seam 142 to the twentieth seam 160. The eighteenth seam 158 attaches the tenth edge 210 of the fourth block 194 to the waist band 105. The nineteenth seam 159 attaches the sixteenth edge 216 of the sixth block 196 to the waist band 105. The twentieth seam 160 attaches the first end 131 of the waist band 105 to the second end 132 of the waist band 105.

The twenty second edge 222 of the pocket panel 104 is secured to the right panel 102 using the right hook and loop fastener 112. The twenty sixth edge 226 of the pocket panel 104 is secured to the left panel 103 using the left hook and loop fastener 122. The use of hook and loop fasteners is well known and documented in the apparel manufacturing arts. The right waterproof lining 113 lines the interior surfaces of the right pocket 181. The left waterproof lining lines the interior surfaces of the left pocket 182.

Access into the right pocket 181 is through a channel formed by the right interior arch 111. Access into the left pocket 182 is through a channel formed by the left interior arch 121. The right absorbent pad 171 is inserted into the right pocket 181. The left absorbent pad 172 is inserted into the left pocket 182.

The containment of the right pocket 181 is bounded by the seventh seam 147, the eighth seam 148, and the eleventh seam 151. The containment of the left pocket 182 is bounded by the ninth seam 149, the tenth seam 150, and the thirteenth seam 153. The opening of the right pocket 181 is formed between the twenty second edge 222 of the pocket panel 104 and the face of the right panel 102. The opening of the left pocket 182 is formed between the twenty sixth edge 226 of the pocket panel 104 and the face of the left panel 103.

The following definitions and directional references were used in this disclosure:

Absorbent: As used in this disclosure, absorbent is an adjective that refers to a material that is able to soak up a liquid such as water.

Arch: As used in this disclosure, an arch refers to a curved edge or surface that bounds a definable object or surface.

Arch, Interior: As used in this disclosure, an interior arch is an arch that is formed in the perimeter of area wherein the interior arch forms a convex curve that faces the interior of the area bounded by the perimeter.

Arch, Exterior: As used in this disclosure, an exterior arch is an arch that is formed in the perimeter of area wherein the exterior arch forms a concave curve that faces the interior of the area bounded by the perimeter.

Elastic: As used in this disclosure, an elastic is a material or object that deforms when a force is applied to it and that is able to return to its relaxed shape after the force is removed. A material that exhibits these qualities is also referred to as an elastomeric material.

Elastic Webbing: As used in this disclosure, an elastic webbing is a webbing that contains elastic yarns as some of the yarns that make up the webbing. An elastic webbing is constructed such that the elastic webbing will stretch when a force is applied and will return to its original shape when after the force is removed.

Elastic Yarn: As used in this disclosure, an elastic yarn is a yarn formed from elastomeric materials.

Hook and Loop Fastener: As used in this disclosure, a hook and loop fastener is a fastener that comprises a hook surface and a loop surface. The hook surface comprises a plurality of minute hooks. The loop surface comprises a surface of uncut pile that acts like a plurality of loops. When the hook surface is applied to the loop surface, the plurality of minute hooks fastens to the plurality of loops securely fastening the hook surface to the loop surface. A note on usage: when fastening two objects the hook surface of a hook and loop fastener will be placed on the first object and the matching loop surface of a hook and loop fastener will be placed on the second object without significant regard to which object of the two objects is the first object and which of the two objects is the second object. When the hook surface of a hook and loop fastener or the loop surface of a hook and loop fastener is attached to an object this will simply be referred to as the "hook or loop surface" with the understanding that when the two objects are fastened together one of the two objects will have a hook surface and the remaining object will have the loop surface.

Loin: As used in this disclosure, the loin refers to a region of the human body that comprises the pelvis, the buttocks, and the adjacent sexual organs.

Negative Space: As used in this disclosure, negative space is a method of defining an object through the use of open or empty space as the definition of the object itself, or, through the use of open or empty space to describe the boundaries of an object.

Pocket: As used in this disclosure, a pocket is a small pouch or storage space that is formed into an object. Pockets are often formed by joining a second textile or a second sheeting to a first textile or a first sheeting, respectively, by sewing or heat sealing respectively.

Rectilinear: As used in this disclosure, rectilinear is an adjective that is used to describe an object that: 1) moves in a straight line or lines; 2) consists of a straight line or lines; 3) is bounded by a straight line or lines; or, 4) is otherwise characterized by a straight line or lines.

Relaxed Shape: As used in this disclosure, a structure is considered to be in its relaxed state when no shear, strain, or torsional forces are being applied to the structure.

Seam: As used in this disclosure, a seam is a joining of: 1) a first textile to a second textile; 2) a first sheeting to a second sheeting; or, 3) a first textile to a first sheeting. Potential methods to form seams include, but are not limited to, a sewn seam, a heat bonded seam, an ultrasonically bonded seam, or a seam formed using an adhesive.

Sewn Seam: As used in this disclosure, a sewn seam a method of attaching two or more layers of textile, leather, or other material through the use of a thread, a yarn, or a cord that is repeatedly inserted and looped through the two or more layers of textile, leather, or other material.

Sheeting: As used in this disclosure, sheeting is a material, such as a textile, a plastic, or a metal foil, in the form of a thin flexible layer or layers.

Strap: As used in this disclosure a strap is a strip of leather, cloth, or other flexible material, often with a buckle, that is used to fasten, secure, carry, or hold onto something.

Strip: As used in this disclosure, the term describes a long and narrow object of uniform thickness that appears thin relative to the length of the object. Strips are often rectangular in shape.

Textile: As used in this disclosure, a textile is a material that is woven, knitted, braided or felted. Synonyms in common usage for this definition include fabric and cloth.

Underclothing: As used in this disclosure, underclothing refers to garments that are intended to be worn next to the skin. Underclothing is often worn in conjunction with an outer layer of clothing.

Webbing: As used in this disclosure, a webbing is strong, close woven or knitted fabric that is used for straps or belting. As used in this disclosure, webbing is a fully formed material that is only cut to length for use. Webbing is not formed by cutting broader materials into strips.

The directional references used in this disclosure correspond to the directional references from the perspective of a person when the invention 100 is worn normally. As such, left refers to the direction towards the left side of the person and left refers to the direction towards the left side of the person. Superior refers to the direction towards the head of the wearer and inferior refers to the direction towards the feet of the wearer. Anterior refers to front side of the person and posterior refers to the back side of the person.

With respect to the above description, it is to be realized that the optimum dimensional relationship for the various components of the invention described above and in FIGS. 1 through 8 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventor claims:

1. An undergarment comprising:
a posterior panel, a right panel, a left panel, a pocket panel, a waist band, and a plurality of seams;
wherein the posterior panel, the right panel, the left panel, the pocket panel, the waist band are assembled to form the undergarment using the plurality of seams;
wherein the undergarment is designed to receive and store urine seepage;
wherein the undergarment is formed with one or more pockets;
wherein each of the one or more pockets is formed with an opening;
wherein the posterior panel is a textile that is cut in a rectilinear shape;
wherein the posterior panel is further defined by a first block, a second block, and a third block;
wherein the posterior panel is further defined with a first edge, a second edge, a third edge, a fourth edge, a fifth edge, a sixth edge, a seventh edge, and an eighth edge;
wherein the first block is a rectangular subsection of the posterior panel;
wherein the first block is partially bounded by the first edge, the second edge, the third edge, and the sixth edge;
wherein the second block is a rectangular subsection of the posterior panel;
wherein the second block is partially bounded by the first edge, the seventh edge, and the eighth edge;
wherein the third block is a rectangular subsection of the posterior panel;
wherein the third block is partially bounded by the third edge, the fourth edge, and the fifth edge;
wherein the right panel is a textile that is cut in a rectilinear shape;
wherein the right panel is further defined by a fourth block and a fifth block;
wherein the right panel is further defined with a ninth edge, a tenth edge, an eleventh edge, a twelfth edge, a thirteenth edge, and a fourteenth edge;
wherein the fourth block is a rectangular subsection of the right panel;

wherein the fourth block is partially bounded by the ninth edge, the tenth edge, the eleventh edge, and the twelfth edge;
wherein the fifth block is a rectangular subsection of the right panel;
wherein the fifth block is partially bounded by the ninth edge, the thirteenth edge, and the fourteenth edge;
wherein the left panel is a textile that is cut in a rectilinear shape;
wherein the left panel is further defined by a sixth block and a seventh block;
wherein the left panel is further defined with a fifteenth edge, a sixteenth edge, a seventeenth edge, an eighteenth edge, a nineteenth edge, and a twentieth edge;
wherein the sixth block is a rectangular subsection of the left panel;
wherein the sixth block is partially bounded by the fifteenth edge, the sixteenth edge, the seventeenth edge, and the twentieth edge;
wherein the seventh block is a rectangular subsection of the left panel;
wherein the seventh block is partially bounded by the nineteenth edge, the eighteenth edge, and the nineteenth edge;
wherein the pocket panel is a textile that is cut in a rectilinear shape;
wherein the pocket panel attaches to the right panel and the left panel to form the right pocket and the left pocket;
wherein the pocket panel is further defined by an eighth block and a ninth block;
wherein the pocket panel is further defined with a twenty first edge, a twenty second edge, a twenty third edge, a twenty fourth edge, a twenty fifth edge, a twenty sixth edge, a twenty seventh edge, and a twenty eighth edge;
wherein the eighth block is a rectangular subsection of the pocket panel;
wherein the eighth block forms the right pocket and the left pocket of the garment;
wherein the eighth block is partially bounded by the twenty first edge, the twenty second edge, the twenty sixth edge, the twenty seventh edge, and the twenty eighth edge;
wherein the ninth block is a rectangular subsection of the pocket panel;
wherein the ninth block is partially bounded by the twenty third edge, the twenty fourth edge, and the twenty fifth edge.

2. The undergarment according to claim 1,
wherein the one or more pockets comprises a right pocket;
wherein the right pocket is a pouch;
wherein the right pocket contains a right absorbent pad.

3. The undergarment according to claim 2,
wherein the right pocket further comprises a right hook and loop fastener, a right waterproof lining, and a right absorbent pad;
wherein the right hook and loop fastener secures the right absorbent pad within the right pocket;
wherein the right absorbent pad absorbs and stores the urine seepage;
wherein the right waterproof lining is used to line the interior surfaces of the right pocket;
wherein the right hook and loop fastener is a hook and loop fastening device;
wherein the right waterproof lining is formed from a water impermeable plastic sheeting.

4. The undergarment according to claim 3,
wherein the right panel comprises a right interior arch;
wherein the right interior arch forms the opening into the right pocket;
wherein the right interior arch is formed in the eleventh edge;
wherein the right interior arch is a negative space;
wherein the right interior arch is formed in the shape of an interior arch.

5. The undergarment according to claim 4,
wherein the one or more pockets comprises a left pocket;
wherein the left pocket is a pouch;
wherein the left pocket contains a left absorbent pad.

6. The undergarment according to claim 5,
wherein the left pocket further comprises a left hook and loop fastener, a left waterproof lining, and a left absorbent pad;
wherein the left hook and loop fastener secures the left absorbent pad within the left pocket;
wherein the left absorbent pad absorbs and stores the urine seepage;
wherein the left waterproof lining is used to line the interior surfaces of the left pocket;
wherein the left hook and loop fastener is a hook and loop fastening device;
wherein the left waterproof lining is formed from a water impermeable plastic sheeting.

7. The undergarment according to claim 6,
wherein the left panel comprises a left interior arch;
wherein the left interior arch is formed in the fifteenth edge;
wherein the left interior arch forms the opening into the left pocket;
wherein the left interior arch is a negative space;
wherein the left interior arch is formed in the shape of an interior arch.

8. The undergarment according to claim 7,
wherein the waist band is an elastic webbing;
wherein the waist band is further defined with a first end and a second end.

9. The undergarment according to claim 8, wherein each of the plurality of seams is an individual seam that attaches a portion of a first structure selected from the group consisting of: 1) the posterior panel; 2) the right panel; 3) the left panel; 4) the pocket panel; and, 5) the waist band to a portion of a second structure selected from the group consisting of: 6) the posterior panel; 7) the right panel; 8) the left panel; 9) the pocket panel; and, the waist band.

10. The undergarment according to claim 9,
wherein the plurality of seams comprises a first seam and a second seam;
wherein the first seam attaches the first edge of the posterior panel to the ninth edge of the right panel;
wherein the second seam attaches the third edge of the posterior panel to the seventeenth edge of the left panel.

11. The undergarment according to claim 10,
wherein the plurality of seams comprises a third seam, a fourth seam, a fifth seam, and a sixth seam;
wherein the third seam attaches the eleventh edge of the fourth block to the twenty third edge of the ninth block;
wherein the fourth seam attaches the twenty fourth edge of the ninth block to the tenth edge of the fourth block;
wherein the fifth seam attaches the twenty fourth edge of the ninth block to the sixteenth edge of the sixth block;
wherein the sixth seam attaches the twenty fifth edge of the ninth block to the fifteenth edge of the sixth block.

12. The undergarment according to claim 11,
wherein the plurality of seams comprises a seventh seam, an eighth seam, a ninth seam, and a tenth seam;
wherein the seventh seam attaches the twenty first edge of the eighth block to the face of the right panel;
wherein the eighth seam attaches the eleventh edge of the fourth block to the face of the pocket panel;
wherein the ninth seam attaches the fifteenth edge of the sixth block to the face of the pocket panel;
wherein the tenth seam attaches the twenty seventh edge of the eighth block to the face of the left panel.

13. The undergarment according to claim 12,
wherein the plurality of seams comprises an eleventh seam, a twelfth seam, a thirteenth seam, a fourteenth seam, and a fifteenth seam;
wherein the eleventh seam attaches the twenty eighth edge of the eighth block to the face of the right panel;
wherein the twelfth seam attaches the twenty eighth edge of the eighth block to the sixth edge of the posterior panel;
wherein the thirteenth seam attaches the twenty eighth edge of the eighth block to the face of the left panel;
wherein the fourteenth seam attaches the seventh edge of the second block to the thirteenth edge of the fifth block;
wherein the fifteenth seam attaches the fifth edge of the third block to the nineteenth edge of the seventh block.

14. The undergarment according to claim 13,
wherein the plurality of seams comprises a sixteenth seam, a seventeenth seam, an eighteenth seam, a nineteenth seam, and a twentieth seam;
wherein the sixteenth seam attaches the second edge of the posterior panel to the waist band from the first seam to the twentieth seam;
wherein the seventeenth seam attaches the second edge of the posterior panel to the waist band from the second seam to the twentieth seam;
wherein the eighteenth seam attaches the tenth edge of the fourth block to the waist band;
wherein the nineteenth seam attaches the sixteenth edge of the sixth block to the waist band;
wherein the twentieth seam attaches the first end of the waist band to the second end of the waist band.

15. The undergarment according to claim 14,
wherein the twenty second edge of the pocket panel is secured to the right panel using the right hook and loop fastener;
wherein the twenty sixth edge of the pocket panel is secured to the left panel using the left hook and loop fastener;
wherein the containment of the right pocket is bounded by the seventh seam, the eighth seam, and the eleventh seam;
wherein the containment of the left pocket is bounded by the ninth seam, the tenth seam, and the thirteenth seam.

16. The undergarment according to claim 15, wherein each of the plurality of seams is a sewn seam.

* * * * *